United States Patent
Hsieh et al.

(10) Patent No.: US 7,842,465 B2
(45) Date of Patent: Nov. 30, 2010

(54) IMMUNOCYTOSTAINING METHODS FOR ENHANCED DYE RATIO DISCRIMINATION IN RARE EVENT DETECTION

(75) Inventors: Huangpin Ben Hsieh, Mountain View, CA (US); Nicole H. Lazarus, Sonoma, CA (US); Robert T. Krivacic, San Jose, CA (US); Douglas N. Curry, Palo Alto, CA (US); Richard H. Bruce, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1004 days.

(21) Appl. No.: 11/333,731

(22) Filed: Jan. 17, 2006

(65) Prior Publication Data

US 2007/0166770 A1 Jul. 19, 2007

(51) Int. Cl.
*G01N 33/53* (2006.01)
(52) U.S. Cl. .................... 435/7.1; 436/532; 424/130.1; 424/178.1
(58) Field of Classification Search ................. None
See application file for complete search history.

(56) References Cited

U.S. PATENT DOCUMENTS

| | | | |
|---|---|---|---|
| 4,556,903 A | 12/1985 | Blitchington et al. | |
| 2003/0082105 A1* | 5/2003 | Fischman et al. | 424/9.6 |
| 2004/0071330 A1 | 4/2004 | Curry | |
| 2004/0071332 A1 | 4/2004 | Bruce et al. | |
| 2004/0091483 A1* | 5/2004 | Weimbs et al. | 424/146.1 |

OTHER PUBLICATIONS

Krivacic, Robert T., et al., "A rare-cell detector for cancer", Proceedings of the National Academy of Sciences of the U.S. of America, Jul. 20, 2004, vol. 101, No. 29, pp. 10501-10504.
Curry, D. N., et al., "High-speed detection of occult tumor cells in peripheral blood", Proceeding sof the 26th Annual International Conference of the IEEE EMBS, San Francisco, CA, Sep. 1-5, 2004, pp. 1267-1270.
Hsieh, H. Ben, et al., "High speed detection of circulating tumor cells", *Biosensors & Bioelectronics*, Elsevier Science Publishers, Barking, GB, vol. 21, No. 10, Apr. 15, 2006, pp. 1893-1899.
European Search Report, Application No. 07100507.8-2204; Dated Jun. 12, 2007, Munich, Germany.

* cited by examiner

*Primary Examiner*—N C Yang
(74) *Attorney, Agent, or Firm*—Fay Sharpe LLP

(57) ABSTRACT

A method is provided for preparing a sample containing potential cells of interest and of using a laser of a laser based system for novel excitation and emission collection, and data usage including use of obtained data for direct and ratio based measurements. The prepared sample is configured to emit signals having spectral characteristics sufficient to permit filtering to differentiate and eliminate most false positives from true positives among acquired imaging events, in an imaging system employing a laser spot having a range of diameters from 1 to 20 μm or greater and which excites the fluorescence in a conventional or novel manner. These filtered events may be subsequently imaged and confirmed with another higher resolution device such as a fluorescent microscope in a short amount of time.

17 Claims, 6 Drawing Sheets

IMMUNOCYTOSTAINING METHODS FOR ENHANCED DYE RATIO DISCRIMINATION IN RARE EVENT DETECTION

BACKGROUND

The present application relates to laser based detection systems, and finds particular application in conjunction with low and high-density cell detection and discrimination in blood smears, biological assays, and the like, and will be described with particular reference thereto. However, it is to be appreciated the present concepts will also find application in detection and discrimination of other types of low- or high-density features on various substantially planar surfaces and samples.

Laser based detection systems are widely used in many industries, including printing, bio/life and medical sciences, and are implemented in biochip readers, and laser scanning cytometers, among other detection systems.

In order to achieve high resolution in one category of such devices, laser light is guided through objectives similar to those for microscopes. These objectives utilize multiple lens elements to achieve high magnification and often near- or sub-micron resolution. Since both excitation and emission light are guided through these objectives, the heavy weight of the objectives and their small aperture limits the speed at which the laser light can be moved and thus limits the speed of scanning of a sample.

Fiber Array Scanning Technology (FAST) developed by Palo Alto Research Center (PARC) of Palo Alto, Calif. does not utilize a microscope-type objective. Instead FAST employs a rapid spinning galvanometer or mirror for directing laser light and a large-aperture fiber bundle to collect light emission over a relatively large area. The FAST scanning speed is very high, however, its spatial resolution is currently at a laser spot of approximately 8 μm. Concepts of FAST based systems is described, for example, in published U.S. Patent Applications 2004/0071330 ("Imaging Apparatus and Method Employing a Large Linear Aperture") and 2004/0071332 ("Apparatus and Method for Detecting and Locating Rare Calls") to Bruce et al. (each hereby incorporated in their entirety by reference).

The implication of the relatively low spatial resolution (i.e., several μm) is the inability of FAST to detect detailed cellular structures or staining characteristics. Therefore, detected matter other than true positive cells, which often have similar intensity and size of true positives, can therefore register as a potential hit. Even after some rudimentary filtering, such as size/intensity scrutiny, an undesirably large number of potential hits still need to be investigated, using time-consuming microscopy investigation. The occurrences of these false positive hits strongly depend on sample preparation methodology where present techniques do not result in sufficient spatial resolution of a detected image event to differentiate between a false positive and a true positive when FAST type system is used.

BRIEF DESCRIPTION

A method is provided for preparing a sample containing potential cells of interest and of using a laser of a laser based system for novel excitation and emission collection, and data usage including use of obtained data for direct and ratio based measurements. The prepared sample is configured to emit signals having spectral characteristics sufficient to permit filtering to differentiate and eliminate most false positives from true positives among acquired imaging events, in an imaging system employing a laser spot having a range of diameters from 1 to 20 μm or greater and which excites the fluorescence in a conventional or novel manner. These filtered events may be subsequently imaged and confirmed with another higher resolution device such as a fluorescent microscope in a short amount of time.

DETAILED DESCRIPTION

Figure 1:
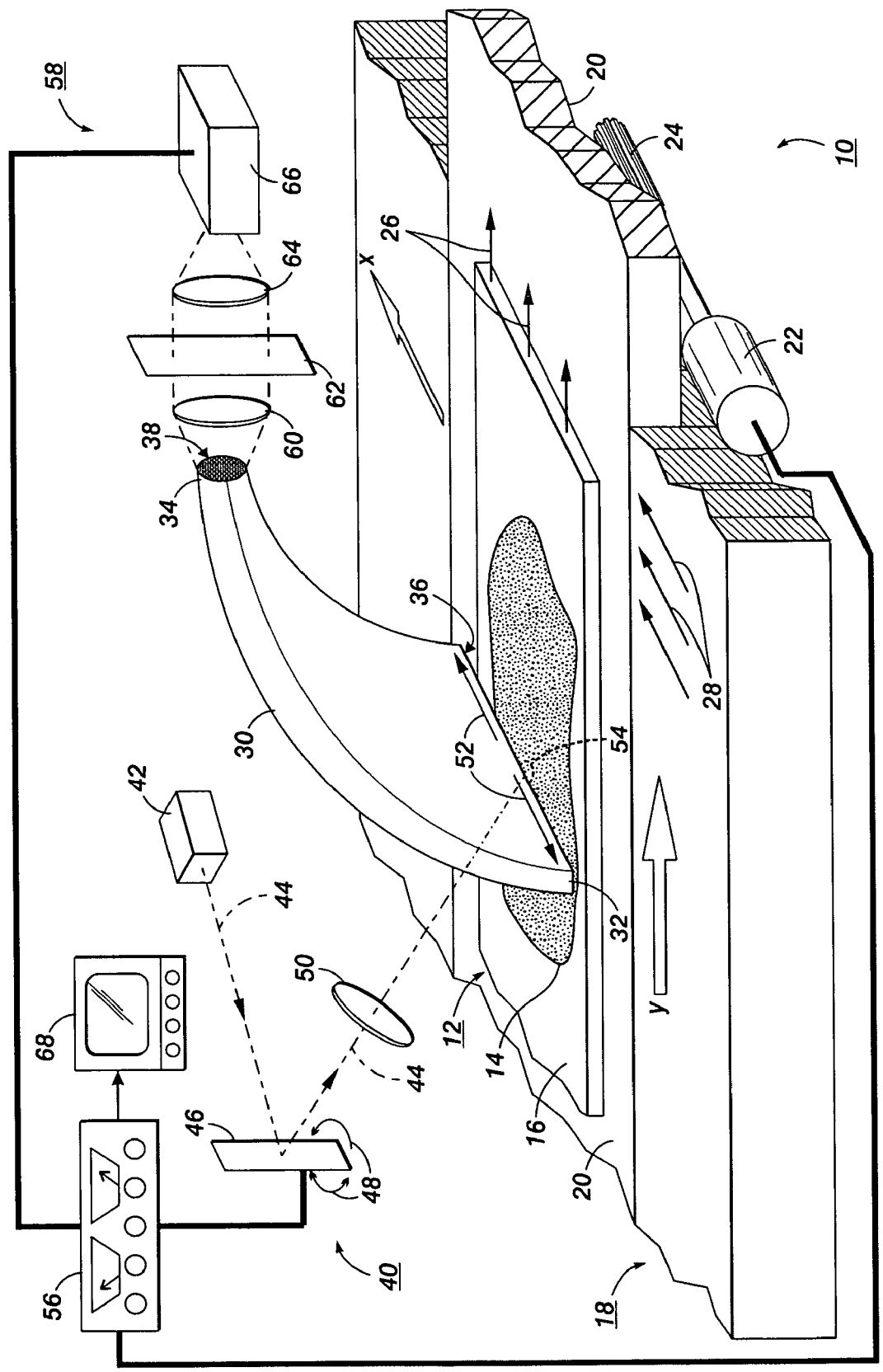
FIG. 1 shows a perspective view of an imaging apparatus formed in accordance with an embodiment of the present application.

With reference to FIG. 1, one embodiment of an imager 10, employing the Fiber Array Scanning Technology (FAST), is depicted. Imager 10 examines a sample 12 with biological smear 14 disposed on at least a portion of a surface of a slide 16.

As is known in the art for cell studies, sample 12 is prepared by drawing a sample of a biological fluid such as, but not limited to, blood or parts of blood from a subject. In a preferred embodiment, the sample is a monolayer of cells adhered to a slide. In particular, blood cells with red cells removed. The fluid sample is treated with a fluorescent material, such as but not limited to a biological marker conjugated to dye fluorophore that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Work is also being undertaken to develop marking materials for numerous cell types from other organs such as brain cells, liver cells, as well as bacteria cells or viruses, among others. The marking material preferably emits a characteristic luminescing output, such as a fluorescence or phosphorescence light, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths. While organic dyes (i.e. fluorphores) are the predominant tagging process, other techniques exist including the use of other markers known as quantum dots and nano-particle probes. Systems using these as well as other materials and techniques may beneficially employ the concepts of the present application.

The smear size will depend on implementation, however, as an example, in a biological fluid, in one situation for a rare cell concentration of about one rare cell of interest per one million cells, the smear 14 might contain one million to 50 million or more cells and occupy an area of about 10 cm² to 100 cm² or greater. Of course, larger or smaller smears can be prepared which are suitable for the anticipated concentration of cells in the sample and the desired minimum measurable cell concentration.

Sample 12 is mounted on an imager translation stage 18 (shown in a partial view) which includes a linearly translatable track 20 that supports sample 12. A motor 22 connects with track 20 via gearing 24 to translate track 20 and the supported sample 12 along a y-direction (indicated by arrows 28) in an x-direction (indicated by arrows 28).

A light pipe 30, such as a fiber optic bundle, includes a first end 32 that is proximate to the sample 12, and a second end 34 that is distal from the sample 12. The first end 32 includes a plurality of first fiber ends arranged substantially parallel to one another in an arrangement that defines a generally linear or high-aspect-ratio rectangular input aperture 36 with a long dimension aligned with the x-direction.

The optical fiber bundle 30 "morphs" or changes cross-sectional dimensions and shape between the first end 32 to the second end 34 such that the second end 34 includes a plurality of second fiber ends that define a compact, generally circular output aperture 38.

A scanning radiation (light) source 40 in a suitable embodiment includes a laser 42 that produces excitation light (radiation beam) 44 at a wavelength or wavelength range selected to excite the marking material used in marking the biological smear 14. The excitation light 44 is angularly scanned by a galvanometer 46 that has a reflective surface that rotates (indicated by curved arrows 48) responsive to an electrical input. An optional focusing lens 50 focuses the angularly scanned excitation light 64 onto the sample 12, and more particularly onto the biological smear 14. The angular scanning produced by the galvanometer 46 translates into a linear sweeping or fast scanning (indicated by arrows 52) of the excitation light, preferably in the form of a spot, which presently is approximately 8 μm or greater in diameter on the biological smear 14 along a linear trajectory 54 arranged below the input aperture 36 and parallel to the long dimension of the input aperture 36.

An electronic control unit 56 communicates with the galvanometer 46 and the translation stage 18 to coordinate the linear sweeping or scanning 52 of the radiation beam 44 along the trajectory 54 and the linear translation 26 of the sample 12 to effectuate a rastering of the radiation beam 44 across a selected area of the sample which is bounded in the x-direction by the smaller of a span of the trajectory 54 and the long dimension of the input aperture 32. Preferably, the span of the trajectory 54 substantially comports with the long dimension of the input aperture 32.

The scanning radiation source 40 and the input aperture 36 are arranged in fixed relative position, the galvanometer 46 provides a linear sweeping of the excitation beam 44 along the x-direction, and the sample 12 is moved by the translation stage 18 linearly along a y-direction to effectuate a two dimensional rastering.

A suitable signal detector 58 is arranged to detect the collected characteristic luminescence emanating from the output aperture 38. A first lens 60 substantially collimates the light, such as but not limited to a laser light. Blocking filter 62 is optionally provided to remove scattered laser light from the collected light.

A second lens 64 may be provided to focus the collimated collected light onto a photodetector arrangement 66 Combining the compact output aperture 38 with focusing optics 60, 64, photodetector 66, which may be a single photodetector, provides signal detection for the spatially distributed linear input aperture 36. Because of the typically low collected characteristic luminescence intensities produced by treated cells, the photodetector 98 is preferably a photomultiplier tube.

Electronic control unit 56 communicates with the galvanometer 46 and the translation stage 18 to raster the radiation beam 44 across the sample. Characteristic luminescence produced by interaction of the radiation beam 44 with treated cells in the biological smear 14 is collected by the input aperture 36, channeled to the output aperture 38 by the optical fiber bundle 30, and detected by the signal detector 58. The electronic control unit 56 receives the detected signal from the photodetector 66, and correlates the detected signal with positional coordinates of the radiation beam 44 on the sample 12.

The electronic control unit 56 suitably formats the detected signal and spatial coordinates information and stores the information in an internal memory, writes the information to a non-volatile storage medium such as a magnetic or optical disk, formats and displays an image representation including an array of picture elements with coordinates mapped to the spatial coordinates information and an intensity or color mapped to the detected signal intensity on a display 68, or the like.

As previously discussed, during the scanning operations, interaction of the spot generated by the laser beam with tagged cells in a sample will cause those tags (or markers) to emit a luminescence, such as a fluorescent light. Commonly, these tags are clustered within the cells and generate high-intensity pixels when they are excited and reemit upon scanning by the radiation spot. For the following discussion, the detected unknown cluster of tags is described as an "image event" to which further investigation is warranted. The size of the radiation spot defines the resolution of the imaging device.

When working with such small structures, noise—such as dirt or dust particles, or miscellaneous cells—may be found on the sample 12, and will have an effect on the acquired image information. Specifically, the imager 10 may accumulate image data irrelevant to the identification of rare cells. At times this noise may be detected as "false positives." It is desirable to eliminate this noise during image acquisition and processing. Therefore, filtering procedures are implemented via electronic control unit 80 and/or other elements of system 10 to eliminate information not related to rare cells. The filtering techniques may use various characteristics of an image event to perform the filtering operations, including the number of pixels, intensity, phase and shape of the image event under consideration.

In one embodiment, an image event may be classified as a non-rare cell (false positive) or a rare cell (true positive) image event by counting the number of pixels of the image event under investigation. Knowing approximate sizes of rare cell tag clusters under investigation, a range can be set to filter out those image events having either a number of pixels less than or greater than the prescribed range. For instance, if the range of rare cells would be known to correlate to a number of pixels in a range of 1 to 12, then image events having a pixel range greater than 12, would be eliminated in a filtering operation.

In another filtering embodiment, the shape of an image event is used to filter non-relevant information. Specifically, in many instances an image event correlating to a rare cell or cluster of rare cells would have a known shape corresponding to the rare cells being imaged, and blurred by the impulse response of the radiation spot. If the detected shape is other than expected for the pertinent rare cell and/or clusters of rare cells, this would indicate the detected image event is noise such as a dust or dirt particle or other irrelevant signal from the sample. To assist in the filtering in this arrangement, known pattern matching software may be implemented in imaging system 10. In this filtering operation, it would be expected not to see an image event that had a finer structure than the spots own resolution size. Particularly, the image event would not be smaller than the spot size, although the structure itself may be smaller.

Still a further filtering process which may be used to identify rare cell image events from non-rare cell image events is by tracking the intensity of the image event under investigation. For example, it would be expected that a higher intensity would be detected for rare cell image events that are in phase with the pixel acquisition phase, and would also provide fewer pixels. Out of phase image events would have their energy shared with several neighboring pixels, thereby providing a smaller intensity per pixel, but more pixels. In addition, in some non-specific binding of tags on cells, i.e., cells not related to the rare cells, may produce image events but these would have a lower intensity than the expected intensity from rare cell binding clusters.

The foregoing describes filtering techniques which may be used to screen for rare cell events (true positives) from the image events detected by the imaging system.

However, while some false positives can be detected and eliminated from consideration by employing the above-described filtering concepts, many of the false positives will not be eliminated since the filtering criteria used cannot be set at too stringent of a level. For example, when the filter employs size/intensity criteria, the specific parameters for the size/intensity values cannot be set at a level where all false positives are eliminated, due to the potential adverse effect on true positives. Particularly, in one situation, staining patterns of occult cancer cells are irregular and are imprecise or unknown and, therefore, would be missed if strict (i.e., narrow) size/intensity criteria were set. Thus, existing filtering techniques are not capable of lowering the amount of false positives which need to be investigated to a manageable amount. One particular reason for this inability is due to insufficient spatial resolution with a FAST-type laser based imaging technique mentioned above.

A manner to address the issue of insufficient spatial resolution in a large view/fast scanning system, such as FAST, is to improve sample preparations in a manner whereby during the detection procedure spectrally distinguishable characteristics of the sample that are unique to true positive cells are emitted.

Thus, in addition to and/or in combination with the above discussed filtering techniques, false positives may be minimized in a FAST based type system by improving the spectral characteristics of the prepared samples, to permit easier discrimination between image events.

In conventional fluorescent microscopy (i.e., non-FAST type imagers), broadband excitation sources (e.g., high pressure mercury arc lamp, xenon lamp) are used with bandpass or longpass filters optimized for exciting specific fluorophores (or dyes), in particular in multiple-color microscopy application. The fluorphore can be pre-conjugated to primary antibody so that when put together they bind to the cellular target (antigen), the whole assembly fluoresces when properly illuminated. Alternatively, a fluorophore-conjugated secondary antibody can be used; this secondary is immunized with the serum from the host in which the primary is raised, so it will specifically target the primary antibody. Using the secondary antibody has the advantage of a brighter signal due to signal amplification because multiple copies of the secondary antibody can bind to a single primary antibody, thereby providing for increased ease of discrimination of image events.

In a laser-based scanning system, the laser spot size is usually in the range of a few to tens of microns. In PARC's FAST system, the spot size is approximately 8 µm or greater in diameter, which is close to the size of a human blood cell (~10 µm) and a typical occult circulating cancer cell. It therefore is not able to provide sub-micron resolution needed to view cellular structural characteristics. Although using raster scanning with a galvanometer in a FAST imager achieves high speed, it is at the expense of this lower resolution—a resolution not sufficient to distinguish whether a particular image event represents a false positive which may be an auto-fluorescent artifact, dye aggregate or a true positive, i.e. a genuinely labeled cellular target.

Thus, the analysis of the size and intensity for a single band of fluorescence and/or use of the discussed filtering techniques alone may not be sufficient for effective false positive elimination, as many other matters could give fluorescence pattern similar to those of true positives, i.e. their Stoke's Shift is similar or identical to that of the fluorphores attached to true positives. Where a Stokes Shift is known to be the difference in wavelength between absorbed and emitted quanta. The emitted wavelength is longer or equal to the incident wavelength due to energy conservation, the difference being absorbed as heat in the atomic lattice of the material.

Other matters which could affect fluorescence patterns include auto fluorescence from the blood sample and tiny dust particles or dye aggregates. For example, it is assumed an anti-cytokeratine primary antibody (mouse anti-human) is used at 1:100 dilution to target potential epithelial (likely cancerous) cells circulating in the blood stream, and a secondary antibody such as Alexa 488-conjugated goat anti-mouse is used at 1:1000 dilution to identify the targeted cells. In a typical sample prepared and scanned by a FAST type imager, thousands or more potential hits or image events may be registered at the regular emission band of Alexa 488, i.e. 525 nm+/−20 nm. However, only a few or perhaps none may be true positives. The differences in intensity and/or spot sizes between true positives and false positives are simply not sufficiently distinct to be distinguishable. This inability to distinguish the false positives results in numerous hours of microscopy investigation to image potentially thousands of these false positives. Therefore, in order to better discriminate true positives from false positives novel strategies in the way the fluorescent antibody conjugates are applied in a sample are implemented, thereby generating additional information to improve the filtering applied to screen out the false positives.

Particularly, improved spectral characteristics of a sample may be achieved by using unconventional excitation and emission methods to eliminate background fluorescence and by employing multiple markers (e.g., dyes, etc.) in various ways that target the same cells to create emission ratio signatures that uniquely identify true positives. An unconventional excitation and emission, in one instance, includes employing a laser and a marker or tag together which does not result in an optimal fluorescing of the marker or tag. In the following discussion, the examples refer to the marker as a fluorophore dye, however it is to be understood other appropriate markers are also appropriate for use in connection with the present concepts.

It is to be appreciated that while the foregoing has discussed the FAST system, the following strategies may be applicable to other luminescent (e.g., fluorescent, etc.) systems that use a single laser for excitation. Furthermore, the described strategies and concepts may also be employed in systems employing two or more lasers to increase the specificity by using the first laser while the other laser(s) are freed-up for exciting other tags for additional information.

Figure 2:
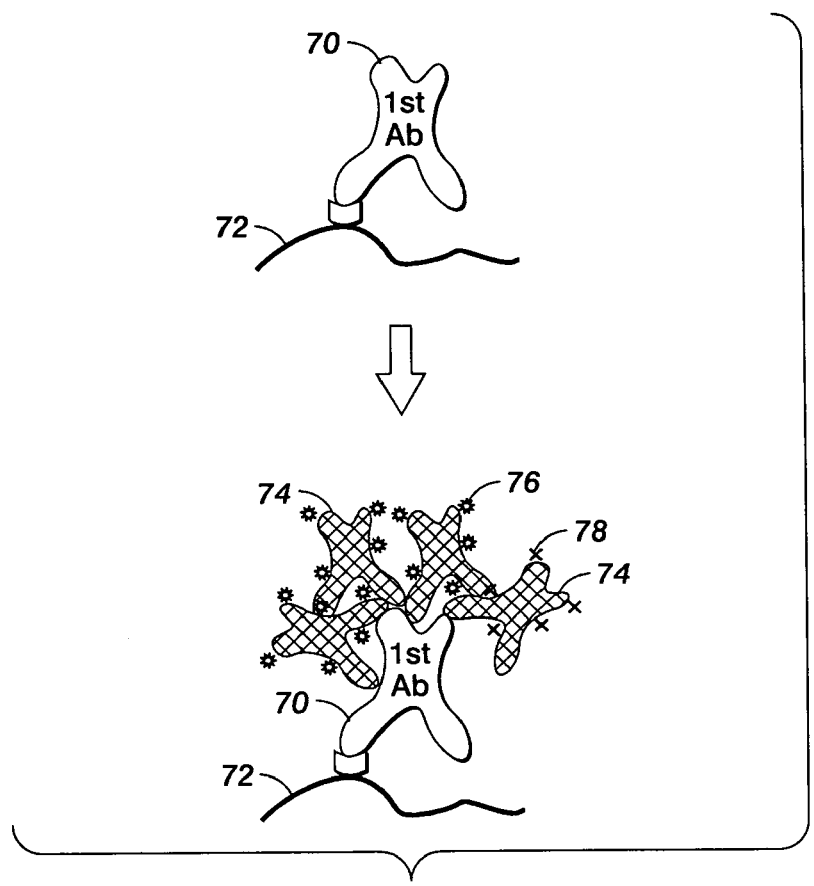
FIG. 2 illustrates a diagram depicting a labeling scheme employing two secondary antibodies in a competitive acquisition method.

In a first implementation illustrated in FIG. 2, instead of using just one fluorophore conjugated (i.e., associated) to the secondary antibody, two are used. Particularly, this procedure illustrates a primary antibody (1$^{st}$ Ab) 70 which is bound to a cellular target 72 of interest, by a known technique. The cellular target being part of material having been placed on a slide with a sample such as in FIG. 1. Then multiple secondary antibodies 74 (of a same type) having two different versions of fluorphores 76(*), 78(+) selectively conjugated thereto. Both the conjugated fluorophores 76, 78 are designed to target the same primary antibody 70.

Figure 3:
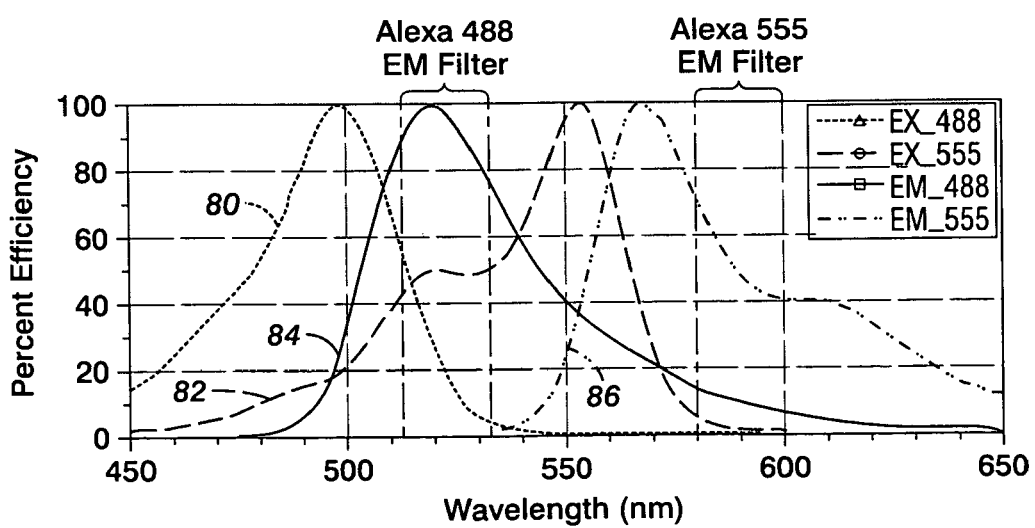
FIG. 3 depicts excitation and emission spectra of Alexa dyes.

When used at different concentrations, their emission intensity reflects the concentration used. For example, Alexa 488 goat anti-mouse and Alexa 555 goat anti-mouse may be used to target and compete for primary mouse anti-human cytokeratin. However, as shown in Table 1 below, which lists quantum properties of selected Alexa dyes, and as illustrated in FIG. 3, which depicts excitation and emission curves of the Alexa dyes 488 and 555, when a 488 nm laser is used, Alexa 488 is excited at much higher efficiency (75.1% according to data from Molecular Probe/invitrogen Corporation of Carlsbad, Calif.) than Alexa 555 (14.2%). In FIG. 3 the excitation and emission spectra of Alexa dyes (EX__488 (80), EX__555 (82), EM__488 (84), and EM__555 (86)) are plotted by absorbance or emission efficiency (Percent Efficiency) versus wavelength (Wavelength (nm)).

TABLE 1

|  | Alexa488 | Alexa555 |
|---|---|---|
| Ex Peak (nm) | 499.0 | 553.0 |
| Em Peak (nm) | 520.0 | 568.0 |
| Exit. Coef. | 7.1E+04 | 1.5E+05 |
| 488 nm Ex. Efcy (%) | 75.1 | 14.2 |

With continuing attention to the first procedure of the present application, to improve the spectral resolution of the sample, a greater amount of Alexa 555 (e.g., 16) antibody (specifically, goat anti-mouse antibody conjugated to Alexa 555) is used than Alexa 488 antibody (e.g., 14). More particularly, Alexa 555 (16) is provided at a concentration ratio of 100:1 as compared to the Alexa 488 (18) antibody. This makes it possible to create an Alexa 555 emission intensity (and/or the amount of emitted photons that can be collected) that's above that of Alexa 488 when excited by the 488 nm laser (such as laser 42 of FIG. 1). Of course other concentration ratios may be applied, in order to create the asymmetric marker arrangement, which provides the desirable spectral resolution.

Further, blood auto fluorescence, for example, would typically have an emission peak around that of Alexa 488 (~525 nm) when excited by a 488 nm laser, and very little or none at that of Alexa 555 (~580 nm). Testing of various cancer cell lines when excited by one 488 nm laser have shown that virtually all of determined true positives have emission intensity ratios (580 nm vs. 525 nm; in the form of average intensity per pixel) greater than 1.0, with the majority of the true positives at 2 or above, when the Alexa 555 dye is used at 100:1 over Alexa 488 dye. The majority of false positives were determined to have a ratio below 1.0. Therefore, "image events" with emission ratios of 1.0 or below may be disregarded and not imaged by the use of a higher resolution device, such as a fluorescent microscope. Some false positives stemming from random aggregates of secondary antibodies or non-specifically bound primary might also have a >1.0 emission ratio and thus will not be filtered out using the above procedure. While the tested cancer cell lines have found the above ratios to be relevant, it is understood other cell lines or patient samples may have different ratios relevant to false positives and true positives. Therefore, for these cell samples, the ratios obtained by testing of these other cell samples would of course be used for filtering.

Thus, by using the above-described "asymmetric" secondary antibody-dye concentrations and selecting an appropriate emission ratio cutoff as a filtering parameter, the amount of false positives are significantly reduced.

Although the above asymmetric concept provides improved detection and elimination of false positives, there are some issues associated with this procedure. Particularly, the low excitation efficiency of Alexa 555 by a 488 nm laser, combined with a bleeding of Alexa 488 emission to Alexa 555 emission area (~580 nm, see the tail of Alexa 488 emission, e.g., EM__488 (84) in FIG. 3) requires the use of a substantially high enough amount of the Alexa 555. Furthermore, in order to avoid a weak signal and therefore non-detection, Alexa 488 concentration cannot be too much lower than a regular or commonly used 1000× dilution. For example, Alexa 488 may be used at a 3000× dilution while Alexa 555 at 30× dilution to substantially ensure a high probability that all true positives have an emission ratio >1.0. However, a 30× dilution of a typical secondary antibody stock (e.g. 2 mg per mL) is considered "very concentrated" which also increases the likelihood of more false positives due to non-specific staining.

A second issue in the asymmetric implementation is that the competitive nature of two secondary antibodies 76, 78 binding to single primary antibody 70 means the results of such bonding can sometimes be less than consistent across different experiments, especially in cells with a low antigen expression level that can be easily saturated.

Figure 4:
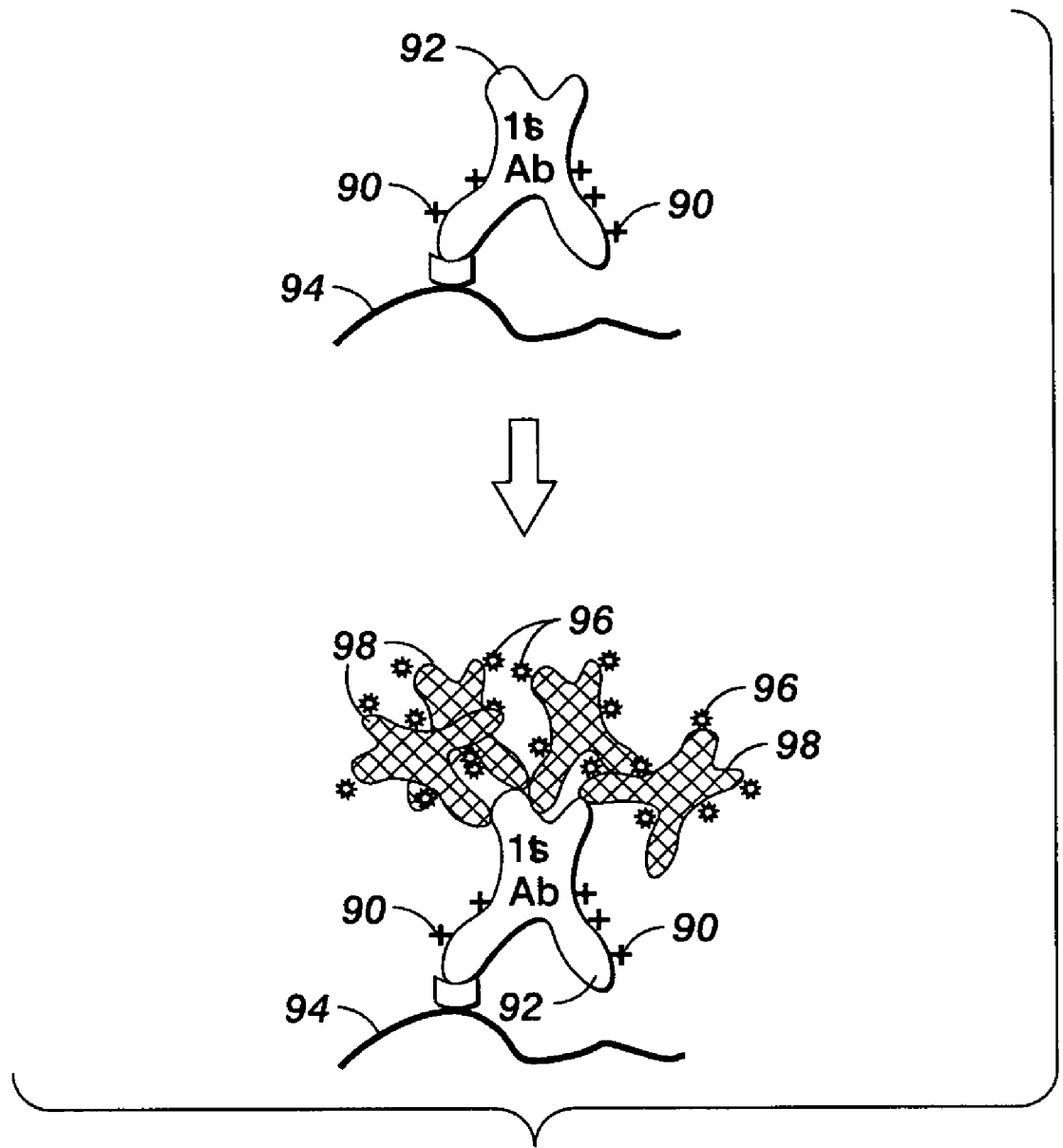
FIG. 4 shows a labeling scheme employing a sequential application of conjugated primary and a conjugated secondary method.

Turning to FIG. 4, depicted is a second approach used to improve the spectral distinctiveness of a sample. In this second approach, instead of using two fluorophore-conjugated secondary antibodies, one (or a first) fluorphore 90(+) is conjugated to a primary antibody 92, which is bound to a cell of interest 94. Another (or second) fluorophore 96(*) is conjugated to a secondary type antibody 98, selected and prepared to target the fluorphore-conjugated primary (or 1$^{st}$ type) antibody 92. As depicted in FIG. 4, this binding is sequential and non-competitive and can be allowed to go to completion.

A specific example of the above employs Alexa 488 mouse anti-human cytokeratin (as the primary antibody) 92 and Alexa 555 goat anti-mouse (as the secondary antibody type) 98. In this scheme, the primary conjugated fluorphore (Alexa 488) 90 is the weaker channel while the signal of the secondary antibody conjugated fluorophore (Alexa 555) 96 is amplified.

Figure 5:
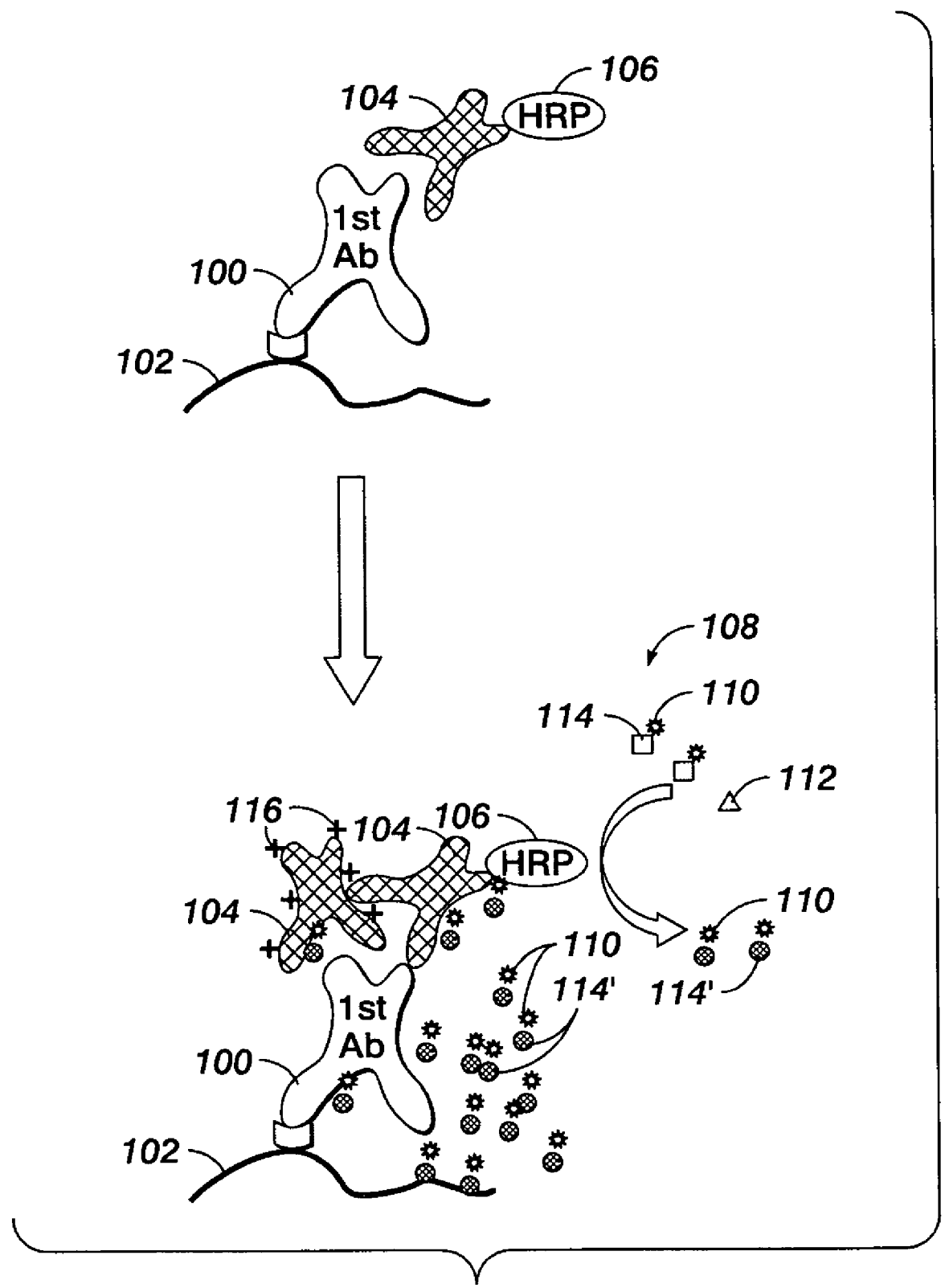
FIG. 5 depicts a labeling scheme which employs Tyramid Signal Application for application of a signal.

Turning to a third approach, instead of using a high secondary antibody concentration for the weakly excited channel (e.g., Alexa 555) as discussed in connection with FIG. 2, the concept shown in FIG. 5 depicts a procedure which uses an enzyme based signal amplification method, such as the Tyramide Signal Amplification (TSA) to amplify the secondary antibody (e.g., Alex 555).

Tyramide Signal Amplification involves using an enzyme to catalyze a chemical reaction that amplifies the signal. In FIG. 5 a non-conjugated primary antibody 100 bound to a cell of interest 102 is used, but instead of regular dye-conjugated $2^{nd}$ antibody, a $2^{nd}$ antibody 104 conjugated to an enzyme horse radish peroxidase (HRP) 106 is used to target the primary antibody 100. Then a reagent 108 containing a marker 110(*), such as a fluorophore dye (e.g., Alexa 555), hydrogen peroxide $H_2O_2$ 112(Δ) and a tyramide mixture 114(□) in a non-reactive form is applied. HRP 106 in the presence of ($H_2O_2$) 112 converts the non-reactive tyramide 114 into a short-lived free-radical tyramide form 114'(●) that deposits in the neighborhood of the site of the bound $2^{nd}$ antibody 104, through binding to nucleophilic protein tyrosine sidechains. This free-radical mechanism allows multiple reactive fluorophore-tyramides (110, 114') to be deposited, thus amplifying the signal from dye 110. The short-lived nature of the converted fluorophore-tyramides (110, 114') means they will not diffuse, and will stay locally close to the $2^{nd}$ types 104. In this scheme, the dye 110 (e.g. Alexa 555) can be amplified many more times than a dye (e.g., Alexa 488) directly conjugated to a second antibody 104.

The present procedure takes advantage of the amplification concepts obtainable via use of TSA to create an asymmetric dye concentration by incorporating the other dye (e.g., Alexa 488) 116 in the form of a conjugate to other secondary antibody 104, at a level different from dye 110, and in a particular embodiment, the amount of dye 116 would be less than the amount of dye 110. While TSA has been cited as the amplification technique, other known biological amplification techniques may also be used.

Figure 6:
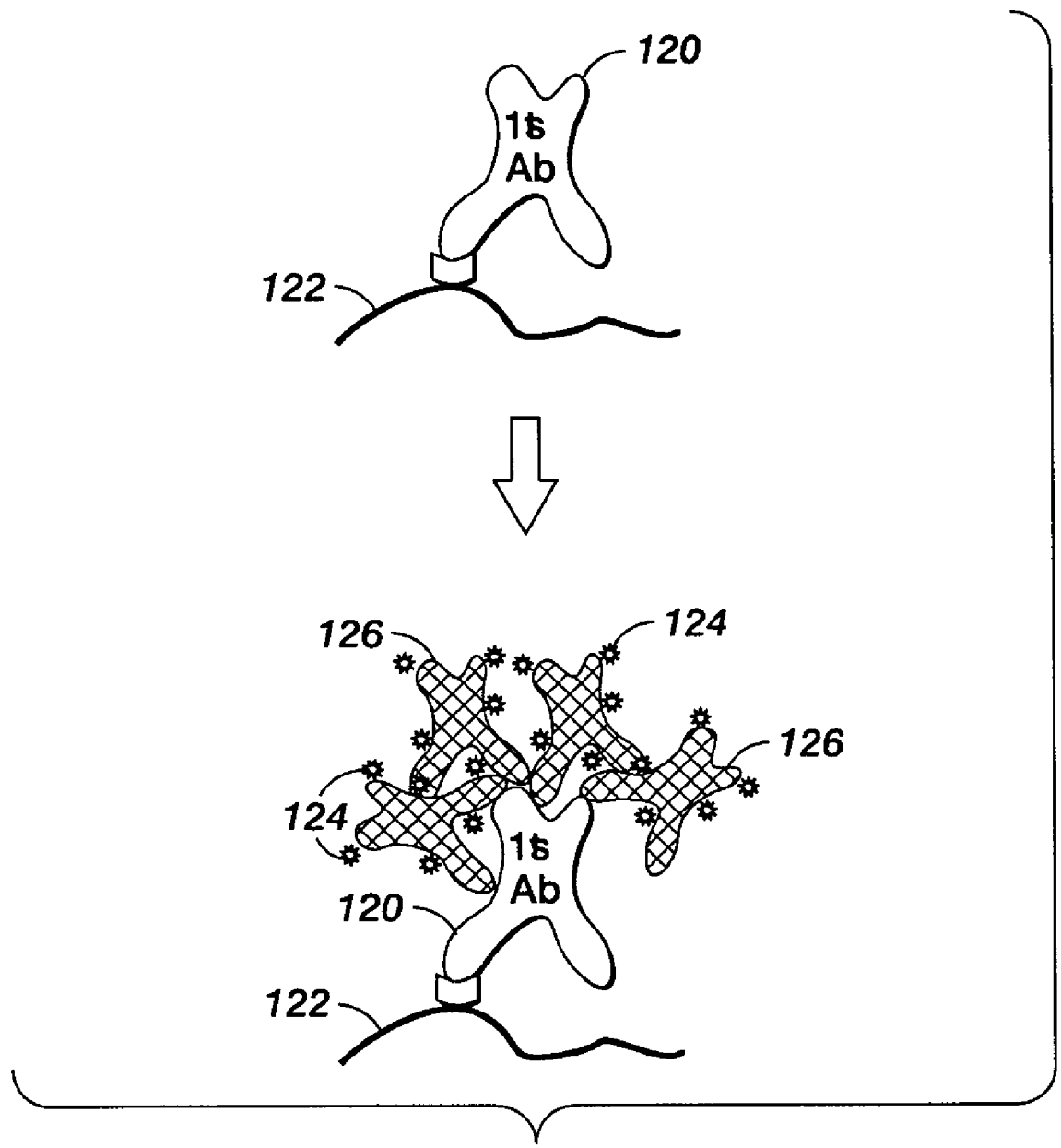
FIG. 6 depicts a further procedure for improving spectral resolution employing a single dye configuration.

Turning to FIG. 6, shown is a further procedure to increase the spectral resolution of a sample. In this example a first type (primary) antibody 120 is, again, bound to a cell of interest 122 using known techniques. This procedure then uses a single fluorophore dye 124 which is associated with a $2^{nd}$ type (secondary) of antibody 126, which itself is configured to target a $1^{st}$ antibody 120. Single dye 124 is excited in a non-conventional manner where the emission is collected and used in a novel way.

In one example, dye 124 may be Alexa 555, and the Alexa 555 conjugated antibody 126 is excited by a 488 nm laser. Since its excitation efficiency with a 488 nm laser is only 14.2% (see Table 1), slightly higher concentrations of Alexa 555 are used. For example, instead of a regular 1000× dilution of the dye, a 150× dilution is used to compensate for the loss in excitation efficiency. The dilution being the dilution of an antibody-dye (or marker) in a buffer (such as phosphate buffered saline) to be applied onto the sample under investigation. More particularly, the dilution is in a range of six to seven times less than the accepted industry standard of approximately 1000× dilution. Then when the Alexa 555 is excited, sufficient fluorescence around its regular emission peak (~585 nm) can be effectively collected by the imaging system. An advantage of this approach is the number of false positives stemming from blood auto fluorescence (i.e., most of which occurs near an emission peak around 525 nm when excited with a 488 nm laser) is dramatically reduced. Since a moderate concentration is used, dye aggregates due to high concentration of antibody are greatly reduced. Through testing of concentration effects using cell lines of various expression levels, false positives can be held to a manageable level while all true positives are detected.

In an alternative procedure, fluorescence of these imaging events may be undertaken and collected at a shorter emission wavelength (e.g. 525 nm when using 488 nm laser) where most autofluorescence occurs. Together with the emission at longer wavelength (e.g. 585 nm for Alexa 555 dye) their ratio provides an additional distinctive set of data for filtering out false positives.

Figure 7:
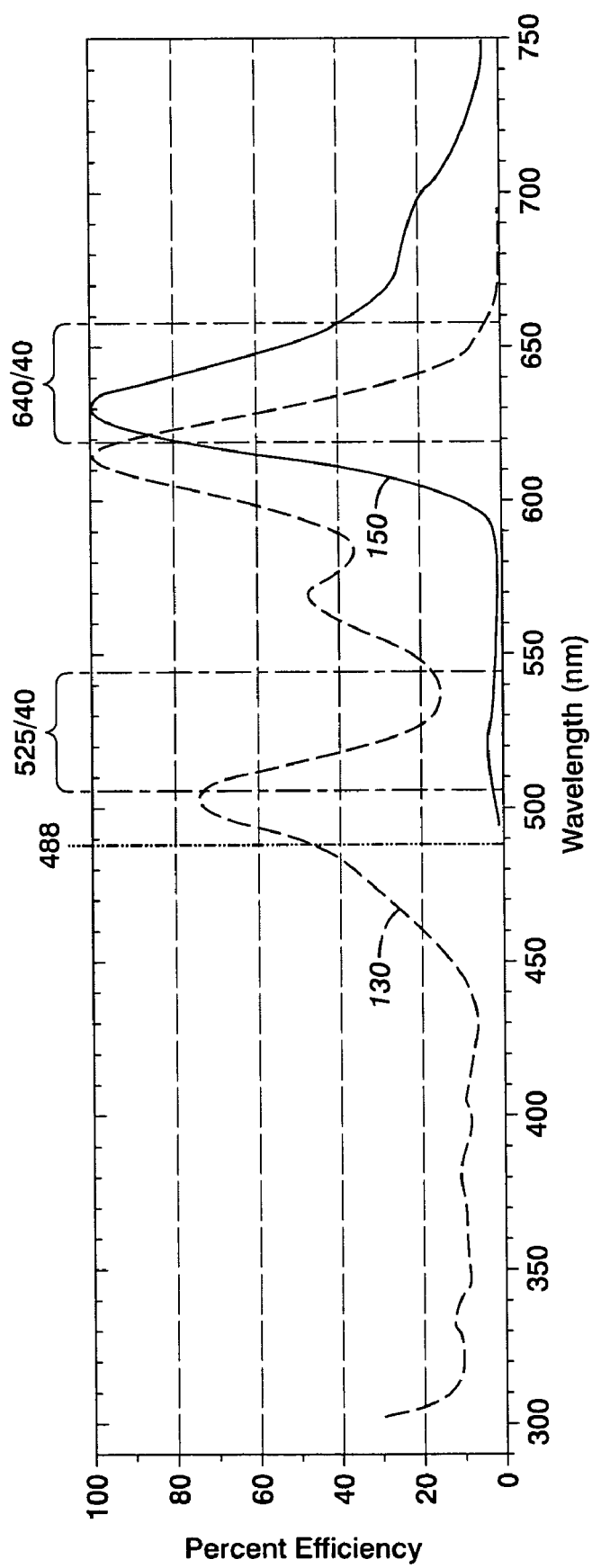
FIG. 7 illustrates the output of the use of a dual dye amplification procedure wherein a ratio of output signals is used for improving the spectral resolution of a sample.

Another sample preparation procedure employs a tandem dye, such as a commercially available tandem dye, DyeMer 488/630 (from Molecular Probes Division of Invitrogen Corporation). For example, FIG. 7 illustrates the absorption curve 130 for the DyeMer 4881630 dye, which shows it excites well at 488 nm besides its main absorption peak around 615 nm; but has most of its emission centered around a peak at 630 nm, as depicted by emission curve 150. Tandem dyes are conjugates of two dyes, with the emission of the first dye being absorbed by the second dye. Though a majority of the emission from the first dye is absorbed, a small percentage can still be emitted in its regular wavelength (i.e., 525 nm for Alexa 488). Therefore, by collecting both emissions around 525 nm and 630 nm, a ratio representing that of the tandem dye, rather than auto fluorescence can be obtained. Coupled with other information such but not limited to as features, size and/or intensity, and by applying a set of filtering criteria, such as those previously discussed in this document, a large number of the false positives from dye aggregates are eliminated.

Using concepts as described above, during laser-based scanning processes, the inventors have achieved a specificity of $10^{-5}$ and better. In other words, for a sample having approximately one (1) million cells, false positives may be limited to just ten (10) cells. These cells (true positives and reduced false positives after filtering) may then be reviewed by a higher resolution detection system such as a microscopic system in a short amount of time.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of preparing a sample containing potential cells of interest, for use in a laser based scanning system designed to detect imaging events which contain the potential cells of interest, the method comprising:
    placing a first material containing the potential cells of interest on a slide;
    adding at least a first type of antibody configured to target the potential cells of interest and allowing binding of the first type of antibody to proceed to completion;
    adding a second type of antibody configured to target the first type of antibody;
    associating at least a first marker or tag, in a first amount, with at least one of the first type of antibody and the second type of antibody; and
    associating a second marker or tag, in a second amount different than the first amount, with at least one of the first type of antibody and the second type of antibody,
    wherein when acted upon by the laser based scanning system, the prepared sample is configured to emit signals having a spectral resolution sufficient to permit filtering to differentiate and eliminate most false positives from true positive imaging event, the filtered imaging events are then confirmed by a higher resolution detection method to determine whether they are truly the cells of interest.

2. The method of claim 1, wherein there are a plurality of the second type of antibody, the first marker or tag associated with a first subset of the plurality, and the second marker or tag associated with a second subset of the plurality.

3. The method of claim 2, wherein the first marker or tag associated with the first subset of the second type of antibody, and the second marker or tag associated with the second subset of the second type of antibody compete for association with the first type of antibody.

4. The method of claim 1, wherein the first marker or tag is associated with the first type of antibody and the second type of marker or tag is associated with the second type of antibody.

5. The method of claim 4, wherein the second type antibody with the associated second marker or tag is targeted to the first type antibody, in a procedure which is a sequential non-competitive manner.

6. The method of claim 1, wherein the first and second markers or tags are each provided in a concentration which is diluted in a range of six to seven times less than an industry understood concentration level for cell detection.

7. The method of claim 1, wherein at least one of the first marker and second marker or tag is Alexa 555 provided at a concentration of approximately 150× dilution.

8. The method of claim 1, wherein at least one of the first marker or tag or the second marker or tag are selected to exhibit a substantially non-optimal excitation for the wavelength of a selected laser of the laser based scanning system to increase spectral differences between the emitted signals.

9. A method of preparing a sample containing potential cells of interest, for use in a laser scanning system designed to detect imaging events which contain the potential cells of interest, the method comprising:
   placing a first material containing the potential cells of interest, on a slide;
   associating a first marker or tag to a first type of antibody;
   associating the first type of antibody to a potential cell of interest; and
   associating a second marker or tag to a second type of antibody, the second type of antibody configured to target the first type of antibody,
   wherein the first marker or tag and second marker or tag are associated with the respective first type of antibody and second type of antibody in a sequential non-competitive manner and wherein when acted upon by the laser based scanning system, the prepared sample is configured to emit signals having a spectral resolution sufficient to permit filtering to differentiate and eliminate most false positives from true positive imaging event, the filtered imaging events are then confirmed by a higher resolution detection method to determine whether they are truly the cells of interest.

10. The method of claim 9, wherein there is a larger number of the second type of antibody with the associated second marker or tag, than the first type of antibody with the associated first marker or tag to increase a spectral difference between signals emitted from the first marker or tag and the second marker or tag, when the sample is scanned by a laser.

11. A method of preparing a sample containing potential cells of interest, for use in a laser scanning system designed to detect imaging events which contain the potential cells of interest, the method comprising:
   placing a first material containing the potential cells of interest on a slide;
   adding a first type of antibody configured to target the potential cells of interest;
   adding a second type of antibody configured to target the first type of antibody;
   associating a first marker or tag with the first type of antibody; and
   associating a second marker or tag with the second type of antibody,
   wherein the first and second markers or tags are provided at a predetermined concentration ratio to create an asymmetric marker or tag arrangement that provides a desired spectral resolution comprising an emission intensity ratio of the first and second markers or tags;
   exciting the first and second markers or tags by the laser based scanning system, causing the markers or tags to emit a first signal from the first marker or tag, and a second signal from the second marker or tag, the first signal and the second signal having spectral differences from each other of a spectral resolution sufficient to permit filtering to differentiate and eliminate false positives from a true positive imaging event and filtering imaging events that fall below a predetermined level of emission intensity ratio; and
   using a higher resolution detection method to determine whether they are truly cells of interest.

12. The method of claim 11 wherein the spectral resolution sufficient to differentiate false positives is achieved using only the first type of antibody and the second type of antibody, the first type of antibody and the second type of antibody being different from each other.

13. The method of claim 11, wherein the second type of antibody targets the first type of antibody and does not target the first marker or tag.

14. The method of claim 11, wherein an amount of the first marker or tag and an amount of the second marker are not equal and are selected to obtain the spectral differences sufficient to permit the filtering to differentiate false positive.

15. The method of claim 11 wherein the placing step includes binding the first type of antibody to the cells of interest.

16. The method of claim 11, wherein the second type of antibody with the associated second marker or tag is targeted to the first type of antibody, in a procedure which is a sequential non-competitive manner.

17. The method of claim 11, wherein at least one of the first marker or tag or the second marker or tag are selected to exhibit less than optimal excitation for a wavelength of a selected laser of the laser based scanning system to increase spectral differences between the emitted first signal and the emitted second signal.

* * * * *